United States Patent
Vasista

(10) Patent No.: US 8,601,438 B2
(45) Date of Patent: Dec. 3, 2013

(54) DATA TRANSFORMATION BASED ON A TECHNICAL DESIGN DOCUMENT

(75) Inventor: Srihari J. Vasista, Bangalore (IN)

(73) Assignee: Accenture Global Services Limited, Dublin (IE)

( * ) Notice: Subject to any disclaimer, the term of this patent is extended or adjusted under 35 U.S.C. 154(b) by 929 days.

(21) Appl. No.: 12/613,281

(22) Filed: Nov. 5, 2009

(65) Prior Publication Data

US 2010/0125828 A1 May 20, 2010

(30) Foreign Application Priority Data

Nov. 17, 2008 (IN) .......................... 2418/MUM/2008

(51) Int. Cl.
*G06F 9/44* (2006.01)
*G06F 9/45* (2006.01)

(52) U.S. Cl.
USPC .......................................... 717/109; 717/136

(58) Field of Classification Search
None
See application file for complete search history.

(56) References Cited

U.S. PATENT DOCUMENTS

| 2003/0106040 A1* | 6/2003 | Rubin et al. ................. 717/106 |
| 2007/0178501 A1* | 8/2007 | Rabinowitz et al. ............. 435/6 |
| 2009/0125892 A1* | 5/2009 | Crewdson ..................... 717/136 |
| 2009/0282065 A1* | 11/2009 | Brimble et al. ............... 707/101 |

OTHER PUBLICATIONS

Examiner's First Report issued in Australian Application 2009/238294 on Jan. 25, 2011.

* cited by examiner

*Primary Examiner* — Hyun Nam
(74) *Attorney, Agent, or Firm* — Harrity & Harrity, LLP

(57) ABSTRACT

Data transformation is initiated by first obtaining a technical design document comprising non-machine-executable expressions of rules for transforming input data into output data. In one embodiment, a graphical user interface is employed to specify how to obtain the technical design document, as well as to designate locations of the input and output data. Thereafter, the technical design document is parsed such that the non-machine-executable expressions of the rules may serve as the basis for generating machine-executable transformation expressions. The resulting machine-executable transformation expressions may be optionally stored and subsequently applied to input data residing in one or more suitable repositories. In this manner, the instant techniques eliminate the need to capture the data transform rules using a data transformation tool, and instead rely on capturing the rules directly from the technical design documents, thereby improving efficiency and accuracy.

15 Claims, 3 Drawing Sheets

DATA TRANSFORMATION BASED ON A TECHNICAL DESIGN DOCUMENT

FIELD OF THE INVENTION

The instant disclosure relates generally to methods for transforming data and, in particular, to techniques for efficiently generating machine-executable transformation expressions based on a technical design document describing the desired data transformations. The instant disclosure also relates generally to devices that can be used for implementing the methods of data transformation. The instant disclosure further relates generally to systems where the methods of data transformation can be implemented.

BACKGROUND OF THE INVENTION

In this so-called information age, transformation of data, i.e., the modification and/or re-arrangement of data from one form into another, has become a ubiquitous task. While many data transformation tasks are relatively straightforward, many others are quite complex and carry significant consequences for failure to correctly transform data as designed. For example, in the pharmaceutical and/or medical device industries, clinical trials are conducted to facilitate the collection of significant quantities of safety and efficacy data for new drugs or devices.

Depending on the type of product and the stage of its development, clinical trials typically enroll healthy volunteers and/or patients into small studies initially, followed by larger scale studies in patients that often compare the new product with the generally accepted, standard course of treatment, i.e., treatment based on currently available pharmaceuticals or devices, if any. Generally, as positive safety data is gathered, the number of patients is typically increased during larger efficacy trials. Regardless of the type and size of a given clinical trial, the data obtained during the clinical trial must to be submitted to the responsible governmental regulatory agency to conduct a thorough review of the new product being developed. For example, in the United States, the Food and Drug Administration (FDA) is responsible for the approval of new drugs and medical devices.

The Clinical Data Interchange Standards Consortium (CDISC) has focused considerable effort on developing standards to help FDA in its review and approval process of safety and efficacy data. This standard format is sometimes referred to as the Study Data Tabulation Model (SDTM) format. There is an increasing demand for transforming data captured during clinical trials (which data can vary widely in its form and content) into the desired SDTM format. Typically, data transformation is divided into two steps: first, data mapping maps data elements from the source to the destination and captures any transformations that must occur and, second, code generation is performed to create the necessary transformation program, i.e., an executable software program that can be run on a computer system. In a typical transformation process, a technical design document, e.g., a metadata-based mapping sheet that specifies how to map input data to output data in accordance with a particular SDTM variable, is created to establish the necessary mapping rules. For example, a technical design document is often captured in the form of a spreadsheet in which individual rows set forth the desired data transformations. Thereafter, a data transformation tool (such as the "TableTrans" visual database programming software by CSS Informatics or the "SAS" Data Integration Studio visual design tool by SAS Institute Inc.) is employed to begin the design of the transformation program. Such design transformation tools employ a graphical user interface (GUI) in which icons representative of various transformational operations may be arranged and ordered as needed in accordance with the transformation rules described in the technical design document. Each icon represents relatively sophisticated data processing functions written in an underlying statistical or database programming language. Because the programs underlying each icon are fully tested, reliable data transformation programs can be devised. That is, by interpreting the arrangements and ordering of the icons established via the GUI, more complex data transformation programs may be generated based on the pre-built functions.

It is not uncommon for a single clinical trial to require 15-20 different data transformation programs created as described above. Given this, the entire process of developing a new study typically requires at least 15-20 days, assuming 3-4 resources working on the transformation programs as described above. Despite the use of the data transformation tools, the overall data mapping process currently remains a tedious process that is sometimes prone to error in capturing the requirements from the technical design document.

While the clinical trial example described above illuminates some of the shortcomings of the prior art, it is understood that these limitations are not the exclusive domain of data transformations employed in clinical trials. Indeed, virtually any endeavor requiring relatively complex data transformations, e.g., data analysis in financial transactions, would suffer from the same shortcomings. Thus, it would be advantageous to provide data transformation techniques, data transformation devices and systems that overcome the limitations of prior art techniques.

SUMMARY OF THE INVENTION

The instant disclosure describes techniques for transforming data that substantially eliminates the need for data transformation tools, as described above. This is accomplished by first obtaining a technical design document comprising non-machine-executable expressions of rules for transforming input data into output data. In one embodiment, a graphical user interface is employed to specify how to obtain the technical design document. The graphical user interface may also be employed to designate locations of the input and output data. Thereafter, the technical design document is parsed such that the non-machine-executable expressions of the rules may serve as the basis for the generation of machine-executable transformation expressions. For example, the machine-executable transformation expressions may comprise suitable query language expressions, as known in the art. The resulting machine-executable transformation expressions may be optionally stored and subsequently applied to input data residing in one or more suitable repositories. In this manner, the techniques described herein eliminate the need to capture the data transform rules using a data transformation tool, and instead relies on capturing the rules directly from the technical design documents, thereby improving efficiency and accuracy. The instant disclosure also describes devices that can be used for implementing the methods of data transformation and further discloses systems where the methods of data transformation and a data transformation device as described above can be implemented.

BRIEF DESCRIPTION OF THE DRAWINGS

The features described in this disclosure are set forth with particularity in the appended claims. These features and attendant advantages will become apparent from consideration of the following detailed description, taken in conjunction with the accompanying drawings. One or more embodiments are now described, by way of example only, with reference to the accompanying drawings wherein like reference numerals represent like elements and in which:

DETAILED DESCRIPTION OF THE PRESENT EMBODIMENTS

Figure 1:
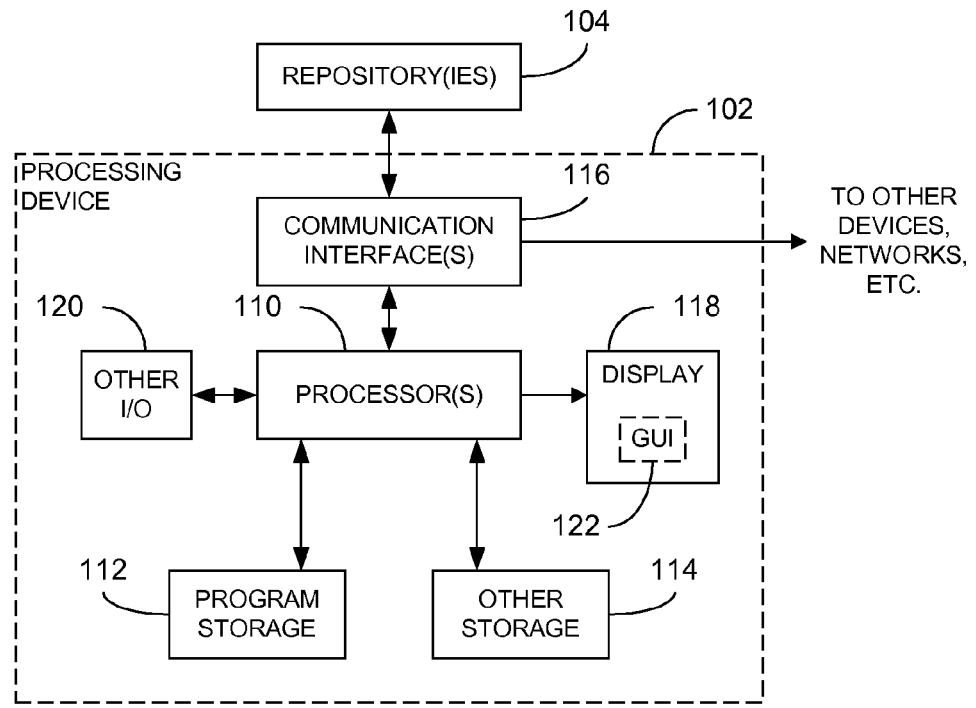
FIG. 1 is a block diagram of the system that may be used for implementing techniques for transforming data in accordance with various embodiments described herein.

Referring now to FIG. 1, a system comprising at least one data transformation device 102 (only one shown for ease of illustration) in communication with one or more repositories 104 is illustrated. Although shown in substantial detail, it is understood that the data transformation device 102 may communicate with the repository(ies) 104 via any convenient communication channel. For example, in one embodiment, the data transformation device 102 communicates with the repository(ies) 104 via one or more suitable networks, including proprietary networks such as local area networks (LANs) and/or public communication networks such as the Internet or World Wide Web. Further still, wireless communication channels may also be employed. Those of skill in the art will appreciate that any of a number of suitable techniques may be employed for this purpose and that the instant disclosure is not limited in this regard.

As shown, the data transformation device 102 comprises at least one processor 110 coupled to one or more storage components 112, 114. For example, in one embodiment, a program storage component 112 is provided and comprises stored, executable instructions for use in controlling operation of the one or more processors 110, whereas another storage component 114 is provided and comprises stored data that may be operated upon the one or more processors 110. Although the program storage component 112 and other storage component 114 are illustrated as being separate from each other, in practice, it is understood that the storage components 112, 114 may be implemented using the same physical devices. For example, the storage components 112, 114 may comprise one or more volatile and/or non-volatile memories including but not limited to random access memory (RAM), read-only memory (ROM), electrically-erasable programmable read-only memory (EEPROM), etc. The one or more processors 110 may comprise a microprocessor, microcontroller, digital signal processor or any other components or combinations thereof capable of executing the stored instructions and operating upon the stored data. Processor and storage arrangements of the type illustrated in FIG. 1 are well known to those having ordinary skill in the art, and various other suitable arrangements may be readily incorporated. For example, the data transformation device 102 may be embodied in a desktop/laptop/handheld computer, a personal digital assistant, a mobile phone, etc. Regardless of the particular type of device 102 employed, such arrangements may be used to implement processing in accordance with the various embodiments described below.

In an embodiment, the device 102 comprises one or more user input/output devices 120, a display 118, and one or more communication interfaces 116, all in communication with the processor(s) 110. The user input/output device(s) 120 may comprise any mechanism for providing user input to, or rendering user output from, the processor(s) 110. For example, in order to accept user input, the device(s) 120 may comprise a keyboard, a mouse, a touch screen, stylus or any other means known to those having ordinary skill in the art. When rendering user output perceivable for the user, the device(s) 120 may comprise a speaker, indicator lights, touch screen, etc. Moreover, the user input/output device(s) 120 may comprise various media drives, such as flash drives, magnetic disc drives and/or optical disc drives. The display 118 may comprise any conventional display mechanism such as a cathode ray tube (CRT), flat panel display, or any other display mechanism known to those having ordinary skill in the art. Techniques for providing display data from the processor(s) 110 to the display 118 are well known in the art. In one embodiment, the display 118 may be used to implement a graphical user interface 122, as known in the art. In particular, operating in conjunction with a user input device 120, the graphical user interface may be used to solicit and receive inputs from a user of the device 102, as described in further detail below. The one or more communication interfaces 116 may comprise hardware and/or software that allows the processor(s) 110 to communicate with the one or more repositories 104 via wired or wireless network, as described above. As further shown, the one or more communication interfaces 116 may also be used to communicate with devices other than the repository (ies) 104, such as other processing devices, networks, email servers, etc. Once again, implementation of such interfaces 116 are well known to those of skill in the art and need not be described in greater detail herein.

The one or more repositories 104 may be implemented using one or more suitably programmed server computers depending on the types of data stored therein. As known in the art, such servers can be co-located or geographically distributed. Alternatively, the at least one repository 104 may include the memory of one or more local computers (e.g., user terminals), whether directly accessible or via a networked environment. Those having ordinary skill in the art will appreciate that virtually any type device capable of storing data may be considered a repository, limited only by the ability of a suitable processing device (e.g., data transformation device 102) to access the data stored thereon. In one embodiment, the data stored on the one or more repositories may comprise data obtained through the conduct of a clinical trial, as described previously. However, it is understood that the instant disclosure is not limited in this regard and that the techniques described herein may be readily applied to any type of data requiring transformation. Regardless of the type of data stored in the repository(ies) 104, the actual form of the data may vary as known in the art, and may include digitally-represented documents, spreadsheets, emails, short message service (SMS) messages, etc. that are generated by various entities. More sophisticated data formats may also be employed such as web pages, web logs, wiki pages, images, videos, etc. In an embodiment particularly applicable to data associated with clinical trials, data may be captured in electronic case report forms (e-CRFs), as known in the art.

Regardless of the particular formats employed, the data stored in the one or more repositories is capable of being analyzed and transformed, as described in greater detail below.

Figure 2:
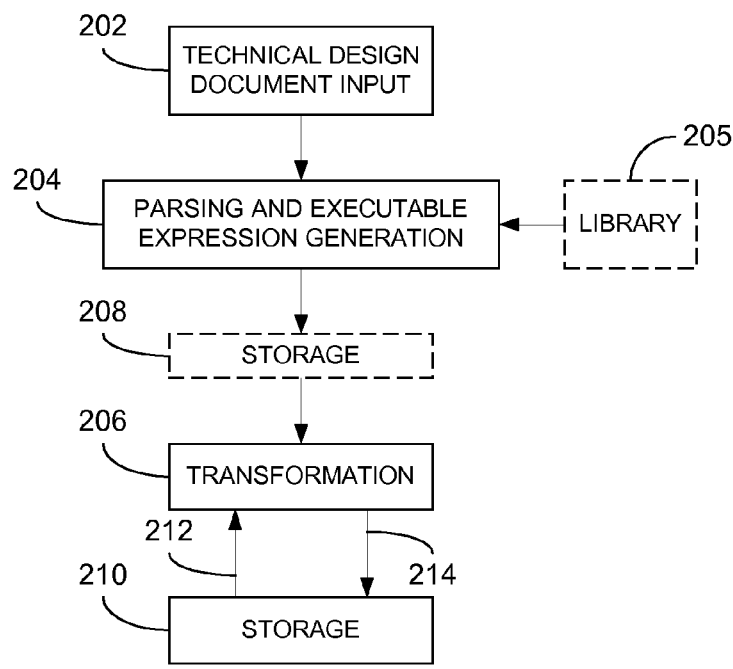
FIG. 2 is a block diagram of an apparatus for transforming data (alternatively referred to as data transformation device) in accordance with various embodiments described herein.

The at least one data transformation device 102 illustrated in FIG. 1 may be used to implement particular structures used in carrying out the techniques described herein. Such structures are illustrated in the example of FIG. 2. In one embodiment, the components 202-206 illustrated in FIG. 2 may be implemented using one or more suitable processors, application specific integrated circuits (ASICs) programmable logic arrays, state machines or any other suitable device known to those having ordinary skill in the art. Techniques for implementing such components 202-206, each comprising the functionality described below, are well known to those having ordinary skill in the art. Likewise, the storage components 208-210 illustrated in FIG. 2 may be embodied by repository(ies) 104 or other storage 114 illustrated in FIG. 1. While the processing device 102 illustrated in FIG. 1 comprises a suitable platform for implementing embodiments of the instant disclosure, those having ordinary skill in the art will further appreciate that other implementation platforms (e.g., application specific circuits (ASICs), programmable logic arrays, state machines, etc.) may be equally employed for this purpose and that the instant disclosure is not limited in this regard.

Figure 5:
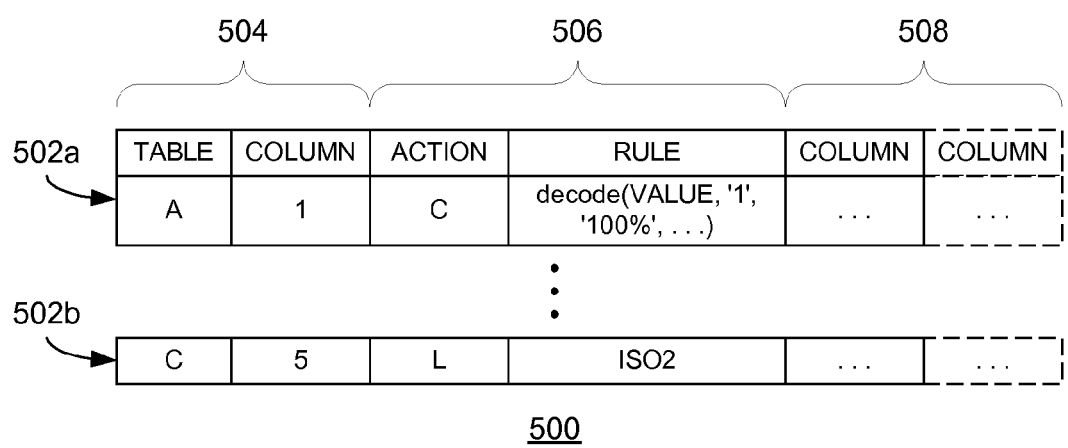
FIG. 5 illustrates an example of a technical design document that may be used in connection with the various embodiments described herein.

As shown, the apparatus of FIG. 2 comprises a technical design document input component 202 in communication with a parsing and executable expression generation component 204. The input component 202 operates to obtain a technical design document for use by the generation component 204. Generally, the input component 202 obtains the technical design document from one or more of storage component 114 or communication interfaces 116 or user input/output devices 120. The technical design document may comprise a digitally stored document comprising non-machine-executable expressions of one or more rules for transforming specified input data into specified output data. For example, the technical design documents may comprise a spreadsheet (such as an "EXCEL" spreadsheet) or other open database capable of being accessed via, for example, java database connectivity (JDBC) or open database connectivity (ODBC) application programming interfaces. Each row of the spreadsheet (or similar structural unit in other types of documents) may comprise a rule expressed in a high-level language that, while descriptive of the rule, is not otherwise capable of being executed by a machine, i.e., in human-readable format only. Expressing rules in this manner allows for quick and intuitive definition of rules without requiring mastery of a particular programming language. A particular example of a suitable technical design document format is described in greater detail below with reference to FIG. 5.

Figure 4:
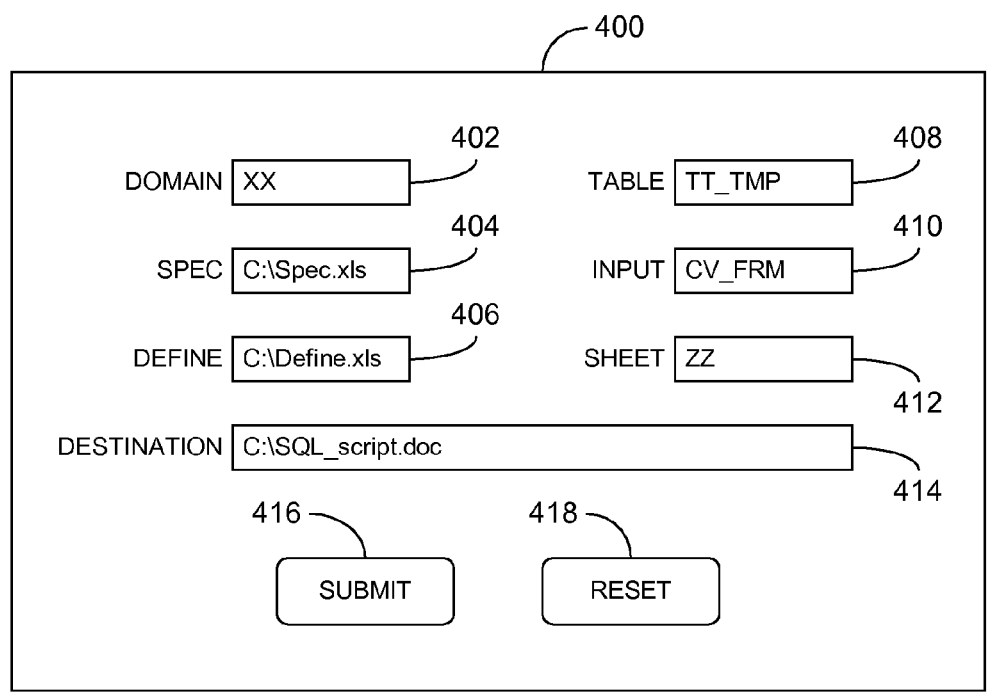
FIG. 4 illustrates an example of a graphical user interface that may be output by the data transformation device employed in connection with the various embodiments described herein.

Given this, the input component 202 may operate on the basis of predetermined knowledge where to find the technical design document, e.g., a known location within, for example, the repository(ies) 104. Alternatively, the input component 202 may provide display data suitable for use in a graphical user interface (such as the example illustrated in FIG. 4, described below) whereby a user of the apparatus may input the necessary information for locating the technical design document, e.g., a uniform resource locator (URL) or functionally similar address information. Techniques for producing display data for use in a graphical user interface are well known in the art.

Once the input component 202 has obtained a technical design document, the generation component 204 may access the technical design document (via, for example, one of the database access modalities noted above) to parse the non-machine-executable expressions of the various rules included therein. Techniques for parsing a document, particularly a spreadsheet or other open database, are well known in the art. Generally, parsing includes traversing the content of the document to identify occurrences of specific symbol strings or tokens, and outputting such tokens. The resulting tokens are then syntactically processed to identify particular expressions corresponding to known operations, which expressions are subsequently semantically analyzed to generate machine-executable transformation expressions or code. When generating machine-executable transformation expressions, the generation component 204 may employ a code library that is internal to or external to the generation component 204. An example of an external code library 205 is illustrated in FIG. 2. In a situation where the code library 205 is external to the generation component 204, the said code library 205 and the generation component 204 may be either co-located (i.e. may form part of a single device) or may be separably located (i.e. may form parts of two or more devices). The code library 205 comprises machine-executable transformation expressions mapped to the non-machine-executable expressions identified via the parsing process. In this manner, instances of non-machine-executable expressions can give rise to machine-executable transformation expressions without the use of an intervening system, such as the data transformation tools described above. While the machine-executable transformation expressions may be drawn from any suitable machine language, in one embodiment, such expressions are drawn from suitable query languages, well-known examples of which include Structured Query Language (SQL) or XQuery.

In an alternative embodiment, described in greater detail below, the technical design document could include machine-executable transformation expressions representative of the transformation rules, in addition to the non-executable expression mentioned above. In this case, the generation component 204 need not parse the machine-executable transformation expressions, but can instead directly incorporate them into its output.

The machine-executable transformation expressions output by the generation component 204 are provided to a transformation component 206. The transformation component 206 is in communication with a first storage component 208 that stores both the input data 212 and the output data 214. Optionally, a second storage component 210 may be provided for storage of the machine-executable transformation expressions and subsequent retrieval by the transformation component 206. The transformation component 206 performs the actual execution of the machine-executable transformation expressions. Thus, for example, where the machine-executable transformation expressions comprise query language instructions or code, the transformation component 206 may comprise a suitable database management system (DBMS) such as Inform Database or Oracle clinical database.

Figure 3:
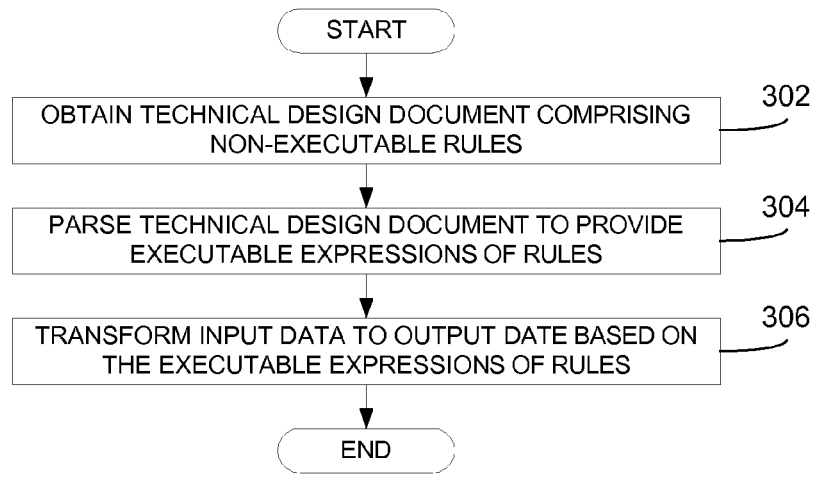
FIG. 3 is a flowchart illustrating processing in accordance with an embodiment described herein.

Referring now to FIG. 3, a flowchart illustrating processing in accordance with the instant disclosure is shown. The processing illustrated in FIG. 3 may be carried out using the machines illustrated in FIGS. 1 and 2. Regardless, processing begins at block 302 where a technical design document comprising non-machine-executable rules is obtained. As note above, such a document may be obtained either by predetermined knowledge concerning where to locate it, or in response to user input. As further described above, a graphical user interface may be employed for the purpose of soliciting and receiving user inputs. A particular example of a suitable graphical user interface 400 is illustrated with reference to FIG. 4. As shown, the GUI 400 may comprise a variety of user input fields 402-414 that allow the user to define not only where to obtain the technical design document, but to also specify where to locate the input data and where to place the output data, among other functions.

For example, a domain field 402 is provided that allows the user to specify a domain applicable to the particular input data to be transformed. Generally, a domain is a designation of a particular desired view of the underlying data. For example, in the context of clinical trial data, domains may include "Demographics", "Adverse Events", "Outcomes" or other classifiers of particular relevance to clinical trial data. A specification field 404 allows the user to enter location information, such as an URL or similar location information. In the illustrated example, the technical design document comprises a spreadsheet entitled "Spec" residing on a local C drive. A definition field 406 allows a user to specify a document describing the structure of the technical design document, e.g., input columns, rules, output columns. In this case, the document describing the structure of the technical design document is another spreadsheet entitled "Define."

Entry of information concerning the location of the input data is supported, in this example, by a table field 408, an input field 410 and a sheet field 412. The table field 408 specifies a name of an input table (in this case, a table called "TT_TMP_"). The input field 410 permits entry of a specific input view name, in this example an input view named "CV_FRM". Similarly, the sheet field 412 permits specification of a particular portion of the selected table (assumed, in this case, to comprise one or more "sheets" of a spreadsheet, as known in the art). In a similar vein, a destination field 414 is provided that allows the user to specify a location (here, a text document entitled "SQL_script" that is to be stored on the local C drive) for storing the generated machine-executable transformation expressions (or scripts). As the various fields 402-414 are completed or revised, the user may select from a pair of button widgets 416, 418 whereby the entered data may be either submitted for processing or cleared, respectively.

Regardless of the manner in which the technical design document is obtained, processing continues at block 304 where the technical design document is parsed and analyzed as described above in order to generate the machine-executable transformation expressions needed to transform the input data according to the rules set forth in the technical design document. An example of a technical design document that may be used for this purpose is further illustrated in FIG. 5. In the illustrated example, the technical design document 500 comprises a spreadsheet having multiple rows 502, wherein each row sets forth the particulars of a given data transformation rule. As further illustrated, various columns are provided to specify the input data specification 504, the transformation rule 506 and the output data specification 508. The input data specification 504 is used to filter the data based on domain specified in the domain field 402 and input view (e.g., one of the rows 502 in the technical design document 500) specified in the input field 410. The transformation rule 506 columns, in the illustrated embodiment, comprise an action column and a rule column. The action column sets forth an indicator that may comprise a "L" value or an "C" value. The "L" value indicates that the corresponding rule is expressed as a logical operator that may be parsed as described above to created machine-executable transformation expressions as described above. For example, in the row labeled 502b, the "L" value indicates that the token "ISO2" should be parsed to derive the necessary machine-executable transformation expressions. Alternatively, the "C" value indicates that the expressions listed in the corresponding rule are already machine-executable transformation expressions and may be passed directly to the output. For example, in the row labeled 502a, the "C" value indicates that the expression "decode(VALUE, '1', '100%', ...) should be passed directly through (without parsing, syntactic or semantic analysis, etc.) as output. The output data specification 508 indicates what the columns of SQL input table/view (i.e., the name of the input table/view is specified by the input field 410) need to be transformed into, i.e., the columns indicated by the input data specification 504 of the input view/table needs to be transformed into an output column as specified by the output data specification 508 using the rule/function 506.

Referring once again to FIG. 3, subsequent to generation of the machine-executable transformation expressions, processing continues at block 306 where the specified input data is transformed into the output data through execution of the machine-executable transformation expressions. As noted above, the machine-executable transformation expressions may be stored prior to execution or may be provided directly to the device performing the transformation for immediate execution.

As described above, the instant disclosure provides techniques for more efficiently performing data transformations. This is achieved through direct interpretation of the technical design document describing the desired data transformations, rather than implementing an intermediate step in which data transformation tools are used to generate the executable transformations. For at least these reasons, the above-described techniques represent an advancement over prior art teachings.

While particular preferred embodiments have been shown and described, those skilled in the art will appreciate that changes and modifications may be made without departing from the instant teachings. For example, while reference has been made to applying the above-described techniques to clinical trial data, it is understood that these techniques may be equally applied to a wide variety of data that may require relatively complex transformations, e.g., financial data. It is therefore contemplated that any and all modifications, variations or equivalents of the above-described teachings fall within the scope of the basic underlying principles disclosed above and claimed herein.

What is claimed is:

1. A method comprising:
    obtaining, by a device, a document comprising a first type of expression and a second type of expression for transforming input data in a first format into output data in a second format,
        the first type of expression being different than the second type of expression;
    parsing, by the device, the document to generate a third type of expression,
        the parsing including:
            identifying a plurality of transformation rules;
            identifying, using a first value of a first transformation rule of the plurality of transformation rules, a second value of the first transformation rule,
                the second value being associated with the second type of expression;
            parsing the identified second value to generate the third type of expression;
            identifying, using a first value of a second transformation rule of the plurality of transformation rules, a second value of the second transformation rule,
                the second value of the second transformation rule being associated with the first type of expression; and using the identified second value of the second transformation rule, without parsing the second value of the second transformation rule, to generate the third type of expression; and transforming, by the device, the input data into the output data based on the third type of expression, the output data being in the second format.

2. The method of claim 1, further comprising:
storing the third type of expression.

3. The method of claim 1, where, when parsing the document, the method further comprises:
identifying, within the document, a source of the input data;
identifying, within the document, a destination of the output data; and
generating the third type of expression further based on the source of the input data and the destination of the output data.

4. The method of claim 1, further comprising:
providing a graphical user interface to at least one processing device, where obtaining the document further comprises:
receiving an input, via the graphical user interface, indicating a location of the document; and
obtaining, based on the location, the document.

5. The method of claim 4, further comprising:
receiving an input, via the graphical user interface, indicating a location of the input data; and
obtaining, based on the location of the input data, the input data.

6. The method of claim 5, further comprising:
receiving an input, via the graphical user interface, indicating a location for the output data; and
transmitting the output data to the location for the output data.

7. The method of claim 1, where the third type of expression comprises one or more query language expressions.

8. The method of claim 1, where the plurality of transformation rules are associated with transforming clinical trial data into a standardized format.

9. A device comprising:
a memory to store instructions; and
at least one processor to execute the instructions to:
obtain a document comprising a first type of expression and a second type of expression for transforming input data in a first format into output data in a second format,
the first type of expression being different than the second type of expression;
parse the document to generate a third type of expression,
the one or more processors, when parsing the document, being further to:
identify a plurality of transformation rules;
identify, using a first value of a first transformation rule of the plurality of transformation rules, a second value of the first transformation rule,
the second value being associated with the second type of expression;
parse the identified second value to generate the third type of expression;
identify, using a first value of a second transformation rule of the plurality of transformation rules, a second value of the second transformation rule,
the second value of the second transformation rule being associated with the first type of expression; and use the identified second value of the second transformation rule, without parsing the second value of the second transformation rule, to generate the third type of expression; and transform the input data into the output data based on the third type of expression, the output data being in the second format.

10. The device of claim 9, where the one or more processors are further to:
store the third type of expression.

11. The device of claim 9, where the one or more processors are further to:
provide a graphical user interface,
where the one or more processors, when obtaining the document, are further to:
receive an input, via the graphical user interface, indicating a location of the document; and
obtain, based on the location, the document.

12. The device of claim 11, where the one or more processors are further to:
receive an input, via the graphical user interface, indicating a location of the input data; and
obtain, based on the location of the input data, the input data.

13. The device of claim 11, where the one or more processors are further to:
receive an input, via the graphical user interface, indicating a location for the output data; and
transmit the output data to the location for the output data.

14. The device of claim 9, where the third type of expression comprises one or more query language expressions.

15. A non-transitory computer-readable medium storing instructions, the instructions comprising:
one or more instructions which, when executed by at least one processor, cause the at least one processor to:
a document comprising a first type of expression and a second type of expression for transforming input data in a first format into output data in a second format,
the first type of expression being different than the second type of expression;
parse the document to generate a third type of expression
the one or more instructions to parse the document including:
one or more instructions to identify a plurality of transformation rules;
one or more instructions to identify, using a first value of a first transformation rule of the plurality of transformation rules, a second value of the first transformation rule, the second value being associated with the second type of expression;
one or more instructions to parse the identified second value to generate the third type of expression;
one or more instructions to identify, using a first value of a second transformation rule of the plurality of transformation rules, a second value of the second transformation rule,
the second value of the second transformation rule being associated with the first type of expression; and
one or more instructions to use the identified second value of the second transformation rule, without parsing the second value of the second transformation rule, to generate the third type of expression; and
transform the input data into the output data based on the third type of expression,
the output data being in the second format.

* * * * *

UNITED STATES PATENT AND TRADEMARK OFFICE
CERTIFICATE OF CORRECTION

| | | |
|---|---|---|
| PATENT NO. | : 8,601,438 B2 | Page 1 of 1 |
| APPLICATION NO. | : 12/613281 | |
| DATED | : December 3, 2013 | |
| INVENTOR(S) | : Srihari J. Vasista | |

It is certified that error appears in the above-identified patent and that said Letters Patent is hereby corrected as shown below:

In the Claims:

Please correct Claim 15 (Column 10, Line 36) to read as follows:

obtain a document comprising a first type of expression and a

Signed and Sealed this
Twenty-fourth Day of June, 2014

Michelle K. Lee
*Deputy Director of the United States Patent and Trademark Office*